US008404092B1

(12) United States Patent
Boeke et al.

(10) Patent No.: US 8,404,092 B1
(45) Date of Patent: Mar. 26, 2013

(54) METHOD FOR THE REDUCTION OF CROSS TALK IN MULTIPLEX CAPILLARY ELECTROPHORESIS

(75) Inventors: Bruce Boeke, Ames, IA (US); Mark McClure, Ames, IA (US); Wei Wei, Ames, IA (US); Ho-Ming Pang, Ames, IA (US)

(73) Assignee: Advanced Analytical Technologies, Inc., Ames, IA (US)

( * ) Notice: Subject to any disclaimer, the term of this patent is extended or adjusted under 35 U.S.C. 154(b) by 0 days.

(21) Appl. No.: 13/430,025

(22) Filed: Mar. 26, 2012

Related U.S. Application Data

(60) Provisional application No. 61/468,947, filed on Mar. 29, 2011.

(51) Int. Cl.
*G01N 27/453* (2006.01)

(52) U.S. Cl. .......................... 204/603; 356/344; 359/232
(58) Field of Classification Search .......... 204/600–605; 356/344; 359/232, 601, 609
See application file for complete search history.

(56) References Cited

U.S. PATENT DOCUMENTS

2006/0219559 A1* 10/2006 Ugai et al. .................... 204/601

* cited by examiner

*Primary Examiner* — J. Christopher Ball
(74) *Attorney, Agent, or Firm* — Pierre T. Varineau

(57) ABSTRACT

The invention is a high-throughput multi-capillary system utilizing a 2-dimensional mask onto which the detection windows of the capillaries are lined up in alternating columns and rows. The image of the capillaries is projected onto a 2-dimensional detection system, such as a charge-coupled-detector (CCD) array. Each row and column of the capillary detection windows is imaged in a separate area of the CCD array, which results in reduced cross-talk between capillaries.

5 Claims, 7 Drawing Sheets

US 8,404,092 B1

METHOD FOR THE REDUCTION OF CROSS TALK IN MULTIPLEX CAPILLARY ELECTROPHORESIS

RELATED US APPLICATION DATA

U.S. Provisional Application No. 61/468,947 titled METHOD FOR THE REDUCTION OF CROSS TALK IN MULTIPLEX CAPILLARY ELECTROPHORESIS filed Mar. 29, 2011.

BACKGROUND OF THE INVENTION

1) Field of the Invention

This invention relates to methods for the reduction of cross-talk in multiplex capillary electrophoresis.

2) Description of Related Art

Capillary electrophoresis (CE) instruments use electric fields to separate molecules within narrow-bore capillaries (typically 20-100 µm internal diameter). By applying electrophoresis in a small diameter fused silica capillary column carrying a buffer solution, the sample size requirement is smaller and the speed of separation and resolution is significantly higher relative to slab gel-electrophoresis. UV absorption and laser induced fluorescence are routinely used as the detection system for CE separation.

CE techniques are employed in numerous applications, including DNA sequencing, nucleotide quantification, mutation/polymorphism analysis, SDS-protein separation, and carbohydrate analysis. In order to improve sample throughput, multiple capillaries or channels are used to perform separations in parallel. For example, in one system a beam expander and a cylindrical lens are used to distribute laser light into a thin line that intersects the axes of the capillaries to provide laser induced fluorescent detection for a multiplexed CE system (K. Ueno et al., Anal. Chem., 66, 1424 (1994)). U.S. Pat. No. 5,582,705 used a laser as the excitation light source for fluorescence detection for a multiplexed CE system, while U.S. Pat. No. 6,788,414 revealed a method to perform UV absorption detection in a multiplexed CE system.

With all of the capillaries or channels illuminated at the same time, scattering, refraction, or reflection of light from neighboring channels will affect the detected channel. That is, detection in one capillary can be influenced by light absorption or fluorescence in the adjacent capillaries, thus affecting trace analysis. This phenomenon is referred to as cross-talk between adjacent capillaries. Cross-talk in the range of 1% to 10% and even higher can be observed in the previously mentioned inventions. For accurate analysis, cross-talk needs to be eliminated if possible.

There is therefore a need to reduce or eliminate the potentially negative cross-talk effects for trace analyte detection using CE.

There are several prior art patented techniques to overcome the cross-talk in multiplex capillary systems. For example, U.S. Pat. No. 5,274,240 used a mechanical stage to translate the capillary bundle to observe one capillary at a time. U.S. Pat. No. 5,324,401 used individual optical fibers to collect emission light from each capillary to eliminate cross-talk. U.S. Pat. No. 5,790,727 used a waveguide to collect the fluorescent signal to reduce cross-talk. Although these various implementations of different optical designs in the hardware to reduce the cross-talk are effective, the cost and the complication of these hardware designs are high. There is thus a need to develop simpler less expensive alternate methods of eliminating cross-talk without increasing instrument complexity or cost. This invention has its primary objective fulfilling this need.

BRIEF SUMMARY OF THE INVENTION

The invention is a high-throughput multi-capillary system utilizing a 2-dimensional mask on which the windows of the capillaries are lined up in alternating columns and rows. The fluorescent image or output of the capillary detection windows is projected onto different rows and columns of a 2-dimensional detection system, such as a charge-coupled-detector (CCD) array. The light from each individual capillary detection window is imaged in a separate area of the CCD array, which results in reduced cross-talk between capillaries.

One aspect of the invention is a mask in which capillaries are lined up in two alternating rows such that the detection window of each capillary, n, is positioned in a different row and column than that of any immediately adjacent capillary (n+1, n−1) detection window. For example, in a 10-capillary system, capillaries 1, 3, 5, 7, and 9 are lined up in row 1 of the mask in columns 1, 3, 5, 7, and 9 respectively. Capillaries 2, 4, 6, 8, and 10 are lined up in row 2 of the mask in columns 2, 4, 6, 8 and 10 respectively. Both row 1 and row 2 and columns 1 through 10 are imaged onto two distinct regions of a CCD detector, resulting in 20 distinct image areas on the detector. A preferable embodiment of the invention is a mask in which capillaries are lined up in 3 alternating rows so that any single capillary detection windows does not share the same row or column with any immediately adjacent capillary. For example, in a 10-capillary system, the windows of capillaries 1, 4, 7, and 10 are lined up in row 1 in columns 1, 4, 7, and 10 respectively; the windows of capillaries 2, 5, and 8 are lined up in row 2 in columns 2, 5, and 8 respectively; the windows of capillaries 3, 6, and 9 are lined up in row 3 in columns 3, 6, and 9 respectively. Each separate capillary window in rows 1, 2, and 3, and columns 1 through 10 are imaged onto distinct, separate regions of a CCD detector. Yet another aspect of the invention is a mask in which the windows of capillaries are arranged alternately in at least 4 rows.

Figure 1:
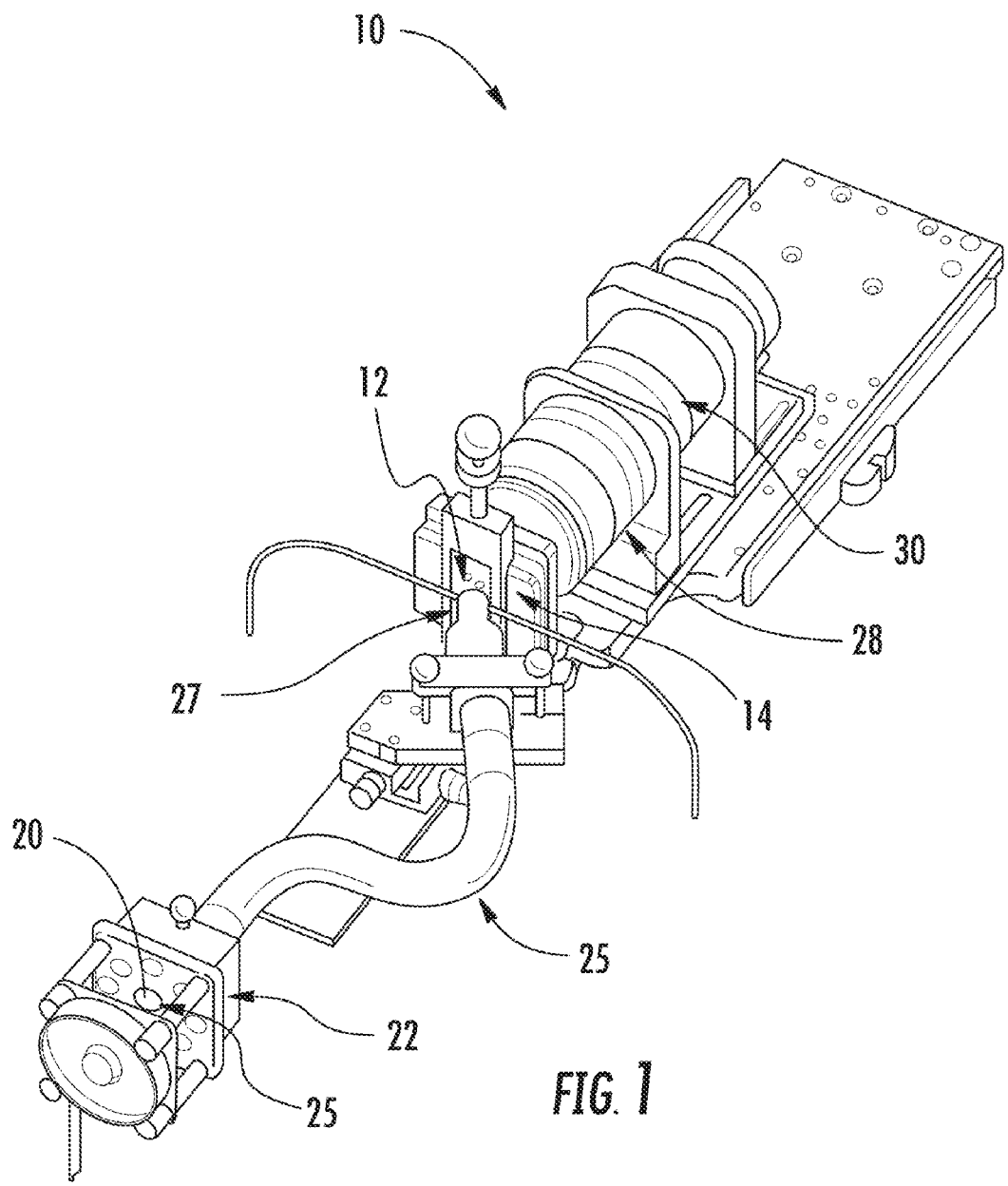
FIG. 1 shows a multiplex capillary electrophoresis detection system of the present invention

obtained with a 96-capillary electrophoresis unit using both the prior art and the present invention.

DETAILED DESCRIPTION OF THE INVENTION

For the purpose of promoting an understanding of the principles of the invention, reference will now be made to the embodiments illustrated in the drawings and specific language will be used to describe the same. It will, nevertheless, be understood that no limitation of the scope of the invention is thereby intended; any alterations and further modifications of the described or illustrated embodiments, and any further applications of the principles of the invention as illustrated therein, are contemplated as would normally occur to one skilled in the art to which the invention relates.

In some embodiments, the invention includes a fluorescence detection system. The detection system includes a plurality of sample vessels or capillaries in which sample is placed. On each capillary or sample vessel, there is a section which is transparent to light, referred to herein as "detection window". A light source is included to emit light to excite a fluorescently labeled sample within each capillary.

Embodiments of the invention also include a fluorescence detector capable of imaging the entire cross section of each capillary, as well as a substantial vertical height of each window. The detector is positioned to detect the fluorescent emissions of the sample.

Other embodiments of the invention include a mask into which the multiple capillaries are placed. The detection windows of capillaries are placed in different rows and columns of the mask, so that the detection window of any one capillary (n) is not adjacent in any row or column to the detection window of any immediately adjacent capillary (n+1) or (n−1).

FIG. 1 shows a fluorescent detection system 10 for multiplexed capillary electrophoresis. The detection system includes a plurality of sample vessels 12 (i.e. capillaries—which in this case is demonstrated by a single capillary), in which sample is placed. The capillaries, 12, are fixed in a mask 14 so that the detection window of any one capillary is not adjacent in any row or column to the detection window of any immediately adjacent capillary. The light source 20, can be a light emitting diode, gas discharge lamp, laser, or incandescent lamp. A high-power LED (1 amp input power) is used as a preferred light source. An optical fiber bundle 25 is optionally used to reshape the light source output from a round shape to a rectangle shape to illuminate and concentrate the light onto all the detection windows of the capillaries simultaneously. A filter 22 is positioned in-between the light source and the optical fiber bundle or, if no optical fiber bundle is used, a filter 22 is positioned in-between the light source and the detection windows of the capillaries. An optical coupler is positioned in-between the light-source 20 and the optical fiber bundle 25. The output of the optical fiber bundle 25 is positioned at an angle from 30 to 70° (27) against the capillary detection windows. Transparent detection windows on capillaries are typically produced by removing a section (about 3 mm in length) of the protective polyimide coating. The output light from the light source 20 or fiber optical bundle 25 illuminates the center of the bare capillary windows simultaneously. The lens 28 collects the scattered fluorescent light from the capillary windows alternately placed into separate rows in the mask and projects the capillary detection window images onto a two-dimensional detector such as a CCD camera 30.

Any appropriate commercial fiber-optic bundle may be used. Two acceptable models are: 1.5"×0.010" Single Branch, Low Profile Line Lights from Edmund Optics Stock No. NT53-986 or a 1.5"×0.020" Dolan Jenner part number QF2036.

Any appropriate optical coupler may be used. Examples include a Dialight part number OPC1-1-COL or a Fraen part number FFLI-07-LL-0.

The detector 30 has the resolution necessary to image distinct parts of the array of capillary detection windows. For example, the detector can have at least one pixel defining the internal volume of each capillary, at least one pixel defining each capillary wall, and at least one pixel defining the space between the capillaries. Furthermore, the detector has a sufficiently large 2-dimensional array so that multiple rows of detection windows can be imaged simultaneously. Any suitable detector may be used. However, detectors such as charge coupled devices (CCDs) are particularly useful with embodiments of the invention. An example of a preferred CCD is made by Starlight Xpress Ltd., model #: SXVR-H9, equipped with an ICX285 CCD chip with 1392 by 1040 pixels in a two-third inch format interline camera and a pixel size of 6.45 microns by 6.45 micron.

The lens 28 has a cross-sectional focus area and depth of field to appropriately focus the light of the entire array of detection windows from the mask 14 to the detector 30. Any suitable lens may be used. An example of a preferable lens is a 35 mm camera lens model HF25HA or model CF25CA from Fujinon.

The detector 30 is attached to a computer system or processor capable of selecting the pixels for the final detection of fluorescent light—whereby only the pixels corresponding to the detection windows of the capillaries are chosen. Pixels corresponding to the capillary walls or the space between capillaries are excluded from the final fluorescent signal. In some embodiments, after the detector (e.g., CCD) records the images, a processor calculates the time lapsed signal-to-noise ratio of the pixels along the x-axis. Accordingly, the processor (e.g., with software) can define the detection regions associated with each capillary detection window. For example, these data discrimination and analysis functions can be written on Labview™ from National Instruments run on a personal computer. Accordingly, embodiments of the invention are useful for imaging multiple capillary detection windows on different rows and columns of an array detector, while excluding stray light from the capillary walls and light from between the capillaries, thereby increasing the signal-to-noise ratio of the illuminated volume to provide a higher quality output.

Figure 2:
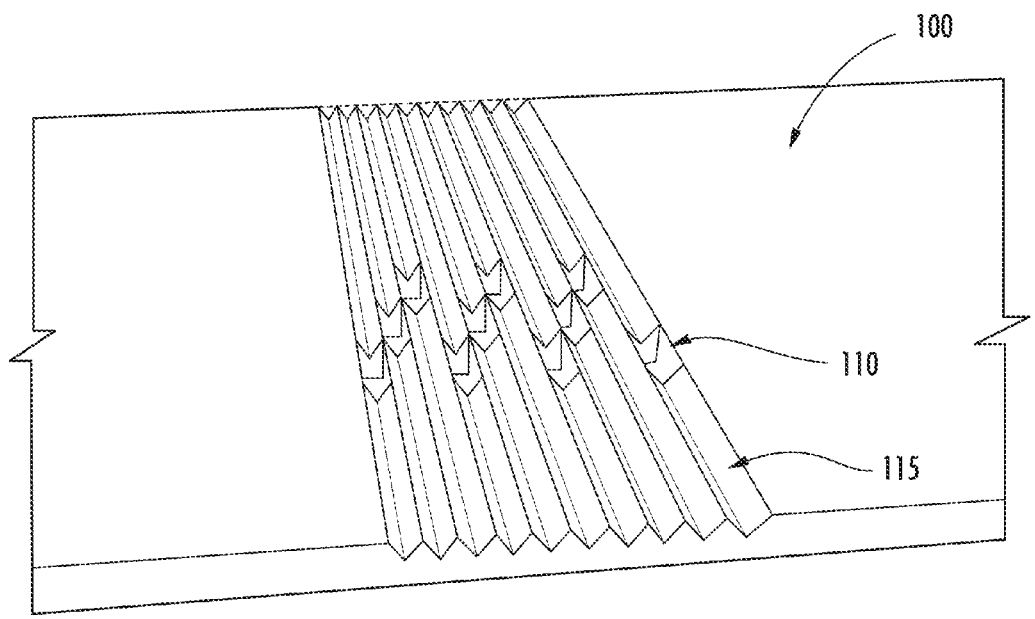
FIG. 2 shows a mask with 3 rows of slots and 11 columns or channels for holding the capillaries.
Figure 3:
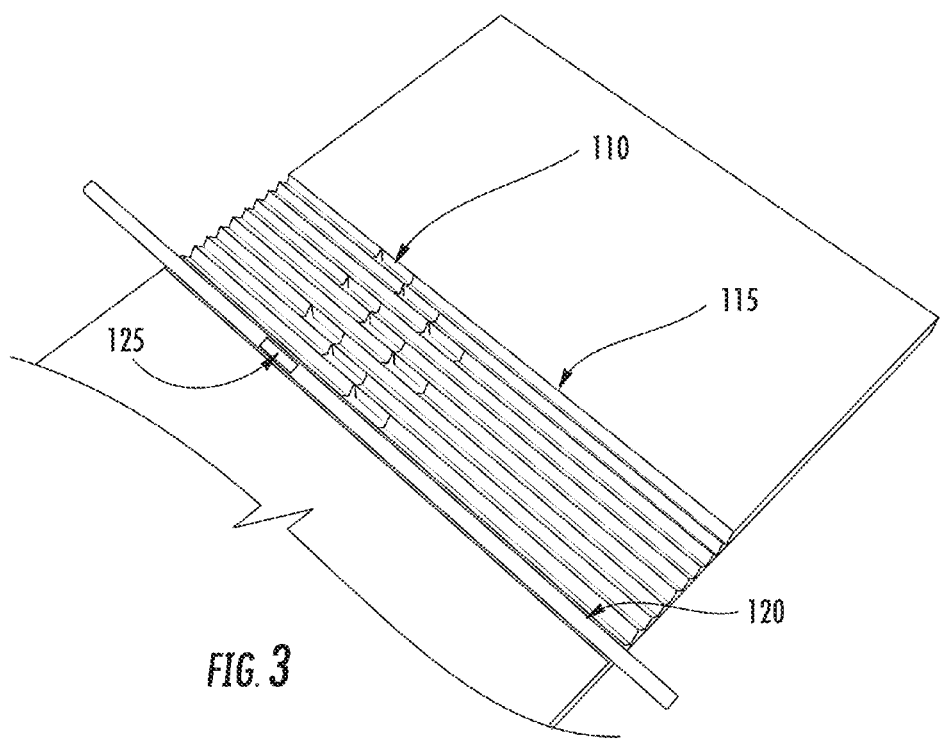
FIG. 3 shows a mask with 3 rows of slots with an example capillary, in which the window of capillary is lined up with a slot in the mask.

FIG. 2 shows a capillary detection window mask 100 with three rows and ten columns of detection window slots 110. In this particular embodiment, triangular grooves as columns 115 are placed in the mask as a means to hold the capillaries in place. It should be noted that grooves or channels to hold the capillaries in place are not a critical part of the invention. Smooth masks without channels or grooves may be used, and the capillaries may be bound appropriately to the surface of these masks by a clamp, glue, or any other binding means. A critical feature of the invention is slots or holes placed in multiple rows and columns in the mask. FIG. 3 shows a top view of the mask in FIG. 2, showing the slots 110 in alternating rows and columns. FIG. 3 shows the mask of FIG. 2 with a sample capillary 120 aligned within a triangular channels 115 showing overlap of the capillary window 125 with the hole or slot in the mask 110. The capillary windows are aligned in a manner such that the detection window of any one capillary (n) is not in the same row or column of the detection window of any immediately adjacent capillary (n+1 or n−1). For example, the detection window of capillary 2 does not share the same row or column of the immediately adjacent capillaries detection windows 1 or 3. The dimension of the detection window slots 110 in the mask may range from 1 micron to 1000 microns in width and 1 micron to 15,000 microns in height. A preferable width is 60 microns and a preferable height is 3 millimeters.

The window mask unit can be constructed from any rigid material, including stainless steel, glass, aluminum, anodized aluminum, titanium, or any appropriate form of plastic, such as poly(propylene), poly(carbonate), poly(ethylene), or ABS resins.

Figure 4:
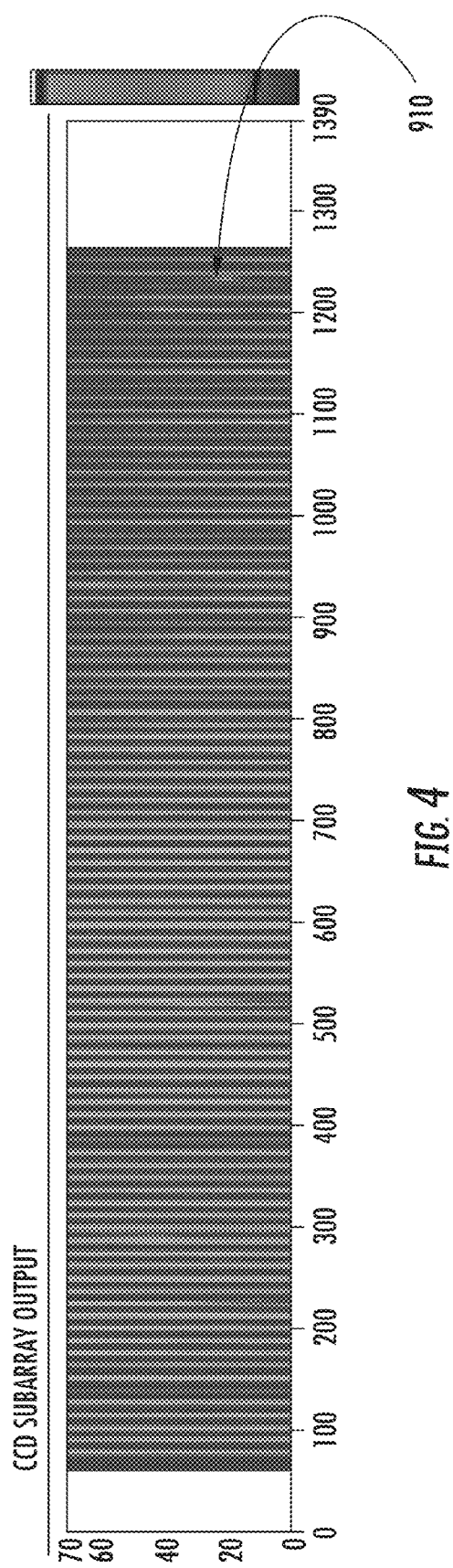
FIG. 4 shows the prior art, in which the fluorescent light of 96 parallel capillaries are captured in a single row on a 2-dimensional CCD array detector.
Figure 8:
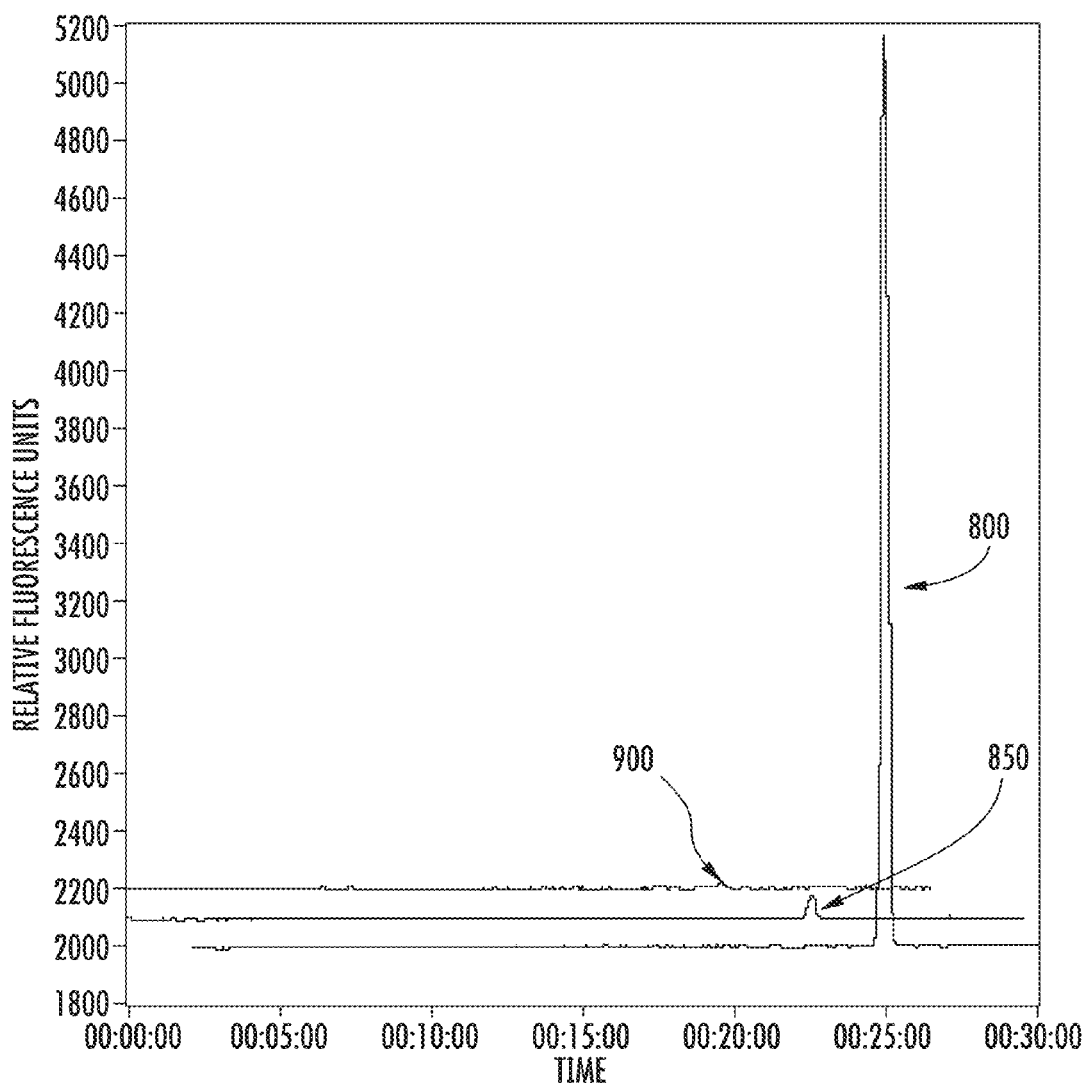
FIG. 8 shows a typical signal electropherogram (n), and the adjacent capillary electropherogram (n+1) (cross-talk)

To illustrate this invention, consider an array of 12 capillaries where the detection windows are placed side-by-side in a single row in 12 columns. In capillary 6, a fluorescent sample passes through the detection window resulting in fluorescent light. This will be referred to the "signal capillary" For all other capillaries; there is no fluorescent sample, which will not result in sample-derived fluorescent light. Light from capillary 6 (n) will interact with the detection windows in the immediately adjacent capillaries 7 (n+1), and 5 (n−1), resulting in florescent scatter, which is detected as an artificial signal in the adjacent capillaries. This phenomenon is signal cross talk. A lesser amount of cross-talk will be detected in capillaries 8 (n+2) and 4 (n−2), 9 (n+3) and 3 (n−3), etc. For a general signal capillary n, cross-talk will be detected at immediately adjacent capillaries n+1 and n−1, and non-immediately adjacent capillaries n+2, and n−2, etc. For a capillary on the edge of the array, cross talk will only be detected at positions n+1, n+2, etc. FIG. 8 shows a typical electropherogram of capillaries (n) 800 and (n+1) 850, showing the signal capillary (n) 800, and cross talk capillary (n+1) 850. FIG. 4 shows the prior-art CCD capture of the fluorescent output of an array of 96 capillary detection windows arranged in a side-by-side fashion of the prior art.

Figure 6:
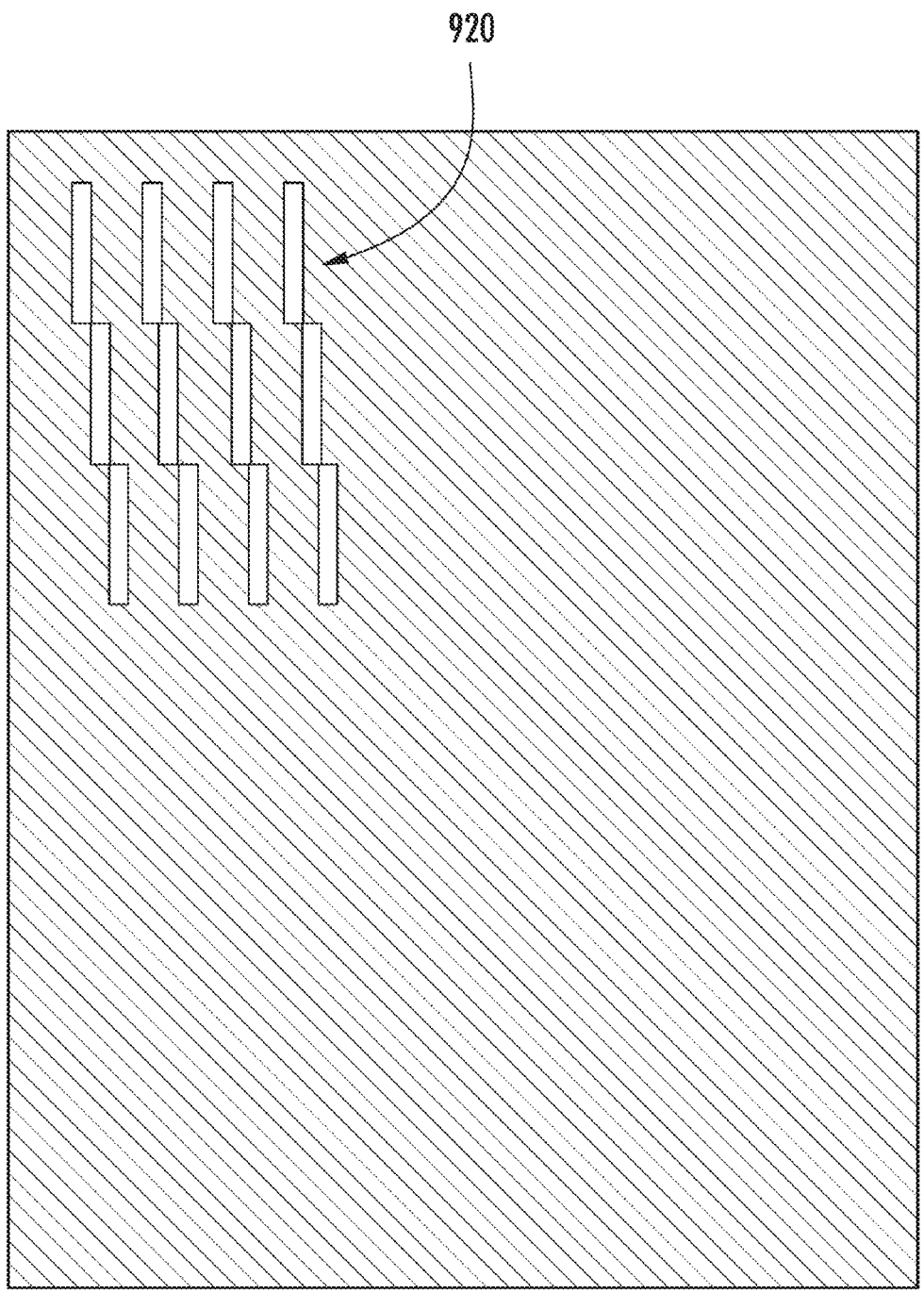
FIG. 6 shows a simulated image according to the present invention, in which the light from 12 capillaries is captured in 3 different rows and 12 different columns onto a 2-dimensional CCD array detector.
Figure 7:
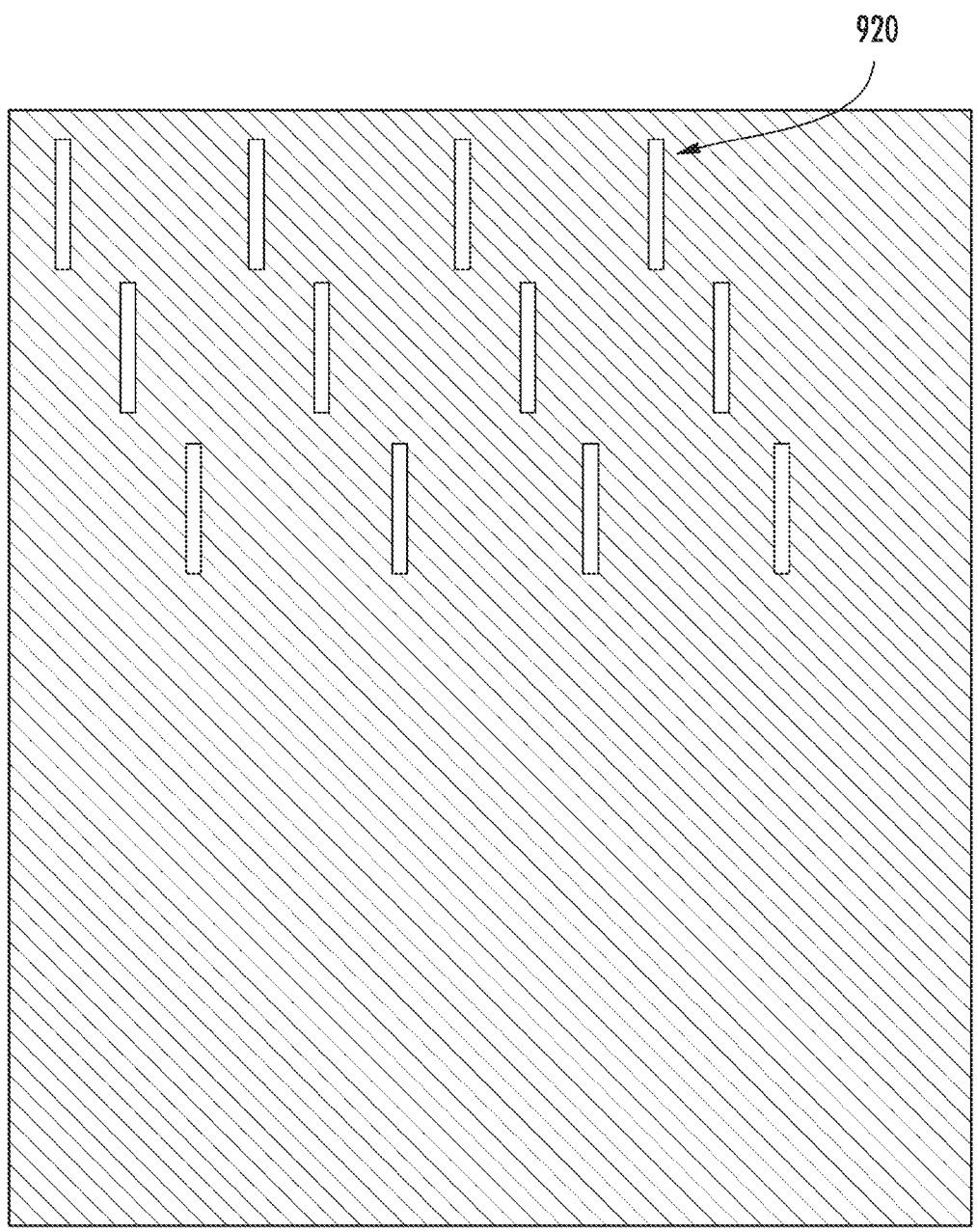
FIG. 7 shows the simulated image according to the present invention, in which the light from 12 capillaries is captured in 3 different rows and 12 different columns onto a 2-dimensional CCD array detector.

Now consider an array of 12 capillaries of the present invention, where the detection windows are placed three different rows and 12 different columns of a mask similar to one shown in FIGS. 2 and 3. Specifically, the detection windows of capillaries 1, 4, 7, and 10 are placed in row 1 of columns 1, 4, 7, and 10 respectively. The detection windows of capillaries 2, 5, 8, and 11 are placed in row 2 of columns 2, 5, 8 and 11. Finally, the detection windows of capillaries 3, 6, 9, and 12 are placed in row 3 of columns 3, 6, 9, and 12 respectively. The simulated light output 920 of these capillary detection windows onto a 2-dimensional array detector is shown in FIGS. 6 and 7. For a signal capillary number 6, significantly reduced cross-talk will be noted in adjacent capillaries 5 and 7, relative to the prior art in which capillary detection windows are aligned next to each other. FIG. 8 shows electropherograms of adjacent capillaries using both the prior art and the present invention. The signal from the signal capillary, n, is shown as electropherogram 800. Cross-talk from capillary n to capillary n+1 using the prior art is shown as electropherogram 850. Cross-talk from capillary n to capillary n+1 using the present invention is shown as electropherogram 900. A window mask of the present invention reduces the cross-talk by over 80% relative to the prior art. A preferred embodiment of the invention uses 3 rows, as shown in FIGS. 2 and 3. For 12 capillaries, 2, 3, 4 or up to 12 rows can be used with 12 columns. For any multiplex capillary system with z capillaries, a desirable configuration is to use a minimum of 3 rows and z columns.

FIG. 4 shows a close-up of prior-art image of the fluorescent output of 96 parallel capillary detection windows 910 imaged onto a 2-dimensional CCD array detector. In this prior-art image, the capillary detection windows are not aligned into separate rows and columns, but rather a single row in multiple columns.

Figure 5:
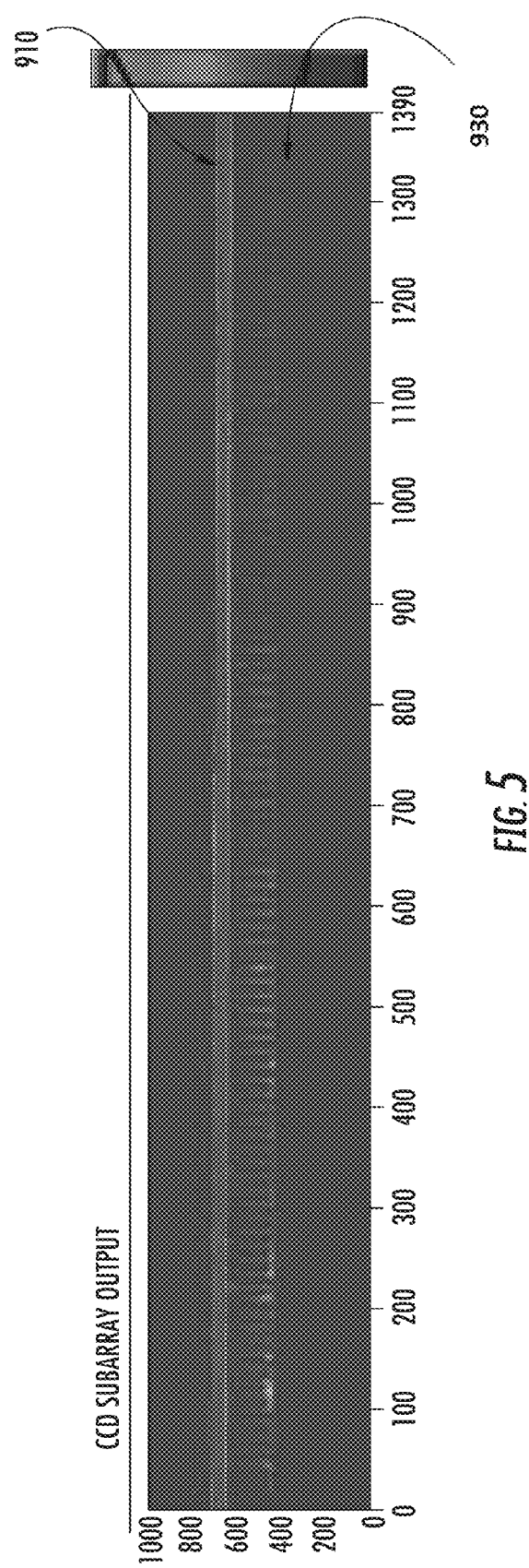
FIG. 5 shows the prior art, in which the fluorescent light of 96 capillaries are captured in a single row on a 2-dimensional CCD array detector.

FIG. 5 shows a prior-art image of a large area of a 2-dimensional CCD detector in which the fluorescent signal output of 96 parallel capillary detection windows 910 is imaged onto a single row onto the CCD array detector 930. Note that most of the area of the CCD detector is unused and that only a single row of array windows utilized.

FIG. 6 shows a simulated image of the invention, in which the fluorescent signal output of 12 parallel capillary detection windows 920 is imaged onto 3 different rows and 12 different columns of a CCD array detector 900.

FIG. 7 shows a simulated image of the invention, in which the fluorescent signal output of 12 parallel capillary detection windows 920 is imaged onto 3 rows and 12 different columns of a CCD array detector, but with a wider spacing of columns relative to FIG. 6.

Example 1

Prior Art: Cross-Talk Observed Using a Standard Side-by-Side Capillary Detection Window Configuration A solution of 10E-6 Molar fluorescein was prepared by diluting 20 microliters of 10E-3 Molar Fluorescein Sodium Salt CAP solution (Fluka 67834) into 20 milliters of de-ionized water. 50 microliters of the 10E-6 Molar solution was placed into a 96 well PCR plate (Axygen PCR-96-FS-C) in column 6 of rows A, B, C, D, E, F, G, and H. Every other well (i.e. all wells not filled with fluorescein solution) of the 96-well PCR plate was filled with 50 microliters of de-ionized water.

The PCR-plate was injected using electrokinetic injection (9 kV, 15 seconds) onto a 96-channel multiplex capillary electrophoresis unit (AdvanCE FS-95 capillary electrophoresis unit, Advanced Analytical Technologies, Incorporated) with the capillaries arranged side-by-side, with separation of no more than 20 micrometers between capillary windows (FIG. 4). A standard capillary electrophoresis gel was used in the capillaries (DNF-910-0350 dsDNA Gel 50-2000 bp, Advanced Analytical Technologies, Inc.) along with a standard running buffer (DNF-455-0300 dsDNA Inlet Buffer, Advanced Analytical Technololgies, Inc.). The capillaries were 50 microns (ID) by 33 centimeters effective length, 55 centimeters (total length). The total run time was 60 minutes at a separation voltage of 9 kV.

Electropherogram peak areas were monitored for each capillary, including the signal capillary (position 6), and each adjacent capillary (n+1, n−1) (position 5, and 7) as well as each (n+2, n−2) adjacent capillary (position 4 and 7). The results are shown in Table 1 and Table 2 below, which demonstrates that significant cross-talk (1.5%) is observed in the immediately adjacent capillaries.

Example 2

Cross-Talk Reduction Using 2-Dimensional Spatial Positioning of Capillary Detection Windows The PCR plate was re-injected into the same electrophoresis unit using the same conditions and reagents as described in Example 1. However, the capillary detection windows were arranged in three rows as described in FIG. 2, where capillary 1 (detection window) was in row 1 column 1, capillary 2 (detection window) was in row 2 column 2, capillary 3 (detection window) was in row 3 column 3, capillary 4 (detection window) was in row 1 column 4 etc. The peak areas of the signal peak, and the adjacent capillaries (n+1, n−1, n+2, n−2)

were measured. The results are shown in Table 1 and Table 2 below, which demonstrates that the signal cross talk was reduced by over 80%, relative to the prior art method in Example 1. Similar data is also shown in FIG. 8, in which the signal capillary peak n 800 is compared with the n+1 capillary for the prior art (850) and the present invention (900)

TABLE 1

Peak area vs capillary position for Example 1 (side-by-side capillary of the prior art) and Example 2 (alternating rows of the current invention).
Capillary, Peak Area Units

|  | n − 2 | n − 1 | n | n + 1 | n + 2 |
|---|---|---|---|---|---|
| Example 1 | 59 | 243 | 13208 | 202 | 48 |
| Example 2 | 8 | 75 | 24832 | 67 | 9.4 |

TABLE 2

Percent cross-talk vs capillary position from Example 1 (side-by-side capillary of the prior art) and Example 2 (alternating rows of the current invention).
Capillary, Percent Cross-talk

|  | n − 2 | n − 1 | N | n + 1 | n + 2 |
|---|---|---|---|---|---|
| Example 1 | 0.45 | 1.84 | 100 | 1.53 | 0.36 |
| Example 2 | 0.03 | 0.30 | 100 | 0.27 | 0.04 |

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is:

1. A multi-capillary electrophoresis detection apparatus having side-by-side capillary detection windows disposed in a plane, a light source positioned to direct a beam of light through each capillary detection window to induce a fluorescent emission from any samples in the capillaries, a light collection lens to direct fluorescent emissions from said samples to a two-dimensional array detector positioned to receive said emissions from said collector lens, the improvement comprising:

arranging said side-by-side capillary detection windows in a two-dimensional mask so that the detection window of any given capillary (n) is positioned in a different row and column than that of any immediately adjacent capillary detection window (n+1, n−1);

and each row contains more than one capillary detection window.

2. The apparatus of claim 1 in which said mask comprises at least two rows and at least four columns; said detection window of each capillary n is in a different row and column from any immediately adjacent capillary n+1 or n−1; and each row contains at least two capillary detection windows.

3. The apparatus of claim 1 in which said mask comprises at least three rows and nine columns said detection window of any capillary n is in a different row and column from any immediately adjacent capillary detection window n+1 or n−1; and each row contains at least three capillary detection windows.

4. The apparatus of claim 1 in which said mask comprises at least four rows and at least sixteen columns; said detection window of each capillary n is in a different row and column from any adjacent capillary n+1 and n−1; and each row contains at least 4 capillary detection windows.

5. The apparatus of claim 1, in which the image of fluorescent light from capillary detection windows of multiple capillaries are projected onto at least two rows and four columns of said two-dimensional array detector and each row contains the projection of at least two capillary detection windows.

* * * * *